(12) United States Patent
Iketani et al.

(10) Patent No.: US 8,996,089 B2
(45) Date of Patent: Mar. 31, 2015

(54) CONTINUOUS ANALYSIS DEVICE AND SAMPLE COMPONENT CONTROL SYSTEM

(75) Inventors: Kazuya Iketani, Kyoto (JP); Koji Katsuki, Kyoto (JP); Yasuhide Kusaka, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 199 days.

(21) Appl. No.: 13/381,574

(22) PCT Filed: Jun. 25, 2010

(86) PCT No.: PCT/JP2010/060895
§ 371 (c)(1),
(2), (4) Date: Dec. 29, 2011

(87) PCT Pub. No.: WO2011/001916
PCT Pub. Date: Jan. 6, 2011

(65) Prior Publication Data
US 2012/0116190 A1 May 10, 2012

(30) Foreign Application Priority Data
Jun. 30, 2009 (JP) .................. 2009-156447

(51) Int. Cl.
*A61B 5/1455* (2006.01)
*A61B 5/1486* (2006.01)
(Continued)

(52) U.S. Cl.
CPC .......... *A61B 5/14865* (2013.01); *A61M 5/1413* (2013.01); *A61M 5/1723* (2013.01);
(Continued)

(58) Field of Classification Search
CPC ............. A61B 5/1455; A61B 5/14553; A61B 5/14552

USPC ................................... 600/310–344
See application file for complete search history.

(56) References Cited

U.S. PATENT DOCUMENTS

| 6,175,752 B1 | 1/2001 | Say et al. ................... 600/345 |
| 7,417,191 B2 | 8/2008 | Mastrototaro et al. .... 174/105 R |

(Continued)

FOREIGN PATENT DOCUMENTS

| JP | 2007-509661 | 4/2007 | .............. A61M 5/20 |
| JP | 2008-246204 | 10/2008 | .............. A61B 5/145 |
| WO | WO 2009/131205 | 10/2009 | .............. A61M 5/20 |

OTHER PUBLICATIONS

International Preliminary Report on Patentability issued Feb. 14, 2012 in corresponding International Application No. PCT/JP2010/060895.

(Continued)

*Primary Examiner* — Eric Winakur
*Assistant Examiner* — Marjan Fardanesh
(74) *Attorney, Agent, or Firm* — Morgan, Lewis & Bockius LLP (57) ABSTRACT

A continuous analysis apparatus capable of transmitting information about components in body fluid to another apparatus such as medicine dosing apparatus more correctly without giving a user displeasure. The continuous analysis apparatus according to the present invention includes a sensing unit 2 including a sensor that is held in subcutaneous tissue for obtaining information with respect to an objective substance in a sample; and a data holding unit 3 having a storage means for storing the information obtained from the sensor or data corresponding to the information, the sensing unit and the data holding unit having configuration so that they are separably joined to each other.

13 Claims, 10 Drawing Sheets

(51) Int. Cl.
*A61M 5/14* (2006.01)
*A61M 5/172* (2006.01)
*A61B 5/00* (2006.01)
*A61B 5/145* (2006.01)

(52) U.S. Cl.
CPC ............ *A61B 5/002* (2013.01); *A61B 5/14532* (2013.01); *A61M 2230/201* (2013.01); *A61B 5/6849* (2013.01); *A61B 2560/0443* (2013.01); *A61B 2560/0475* (2013.01)
USPC ........... 600/344; 600/310; 600/322; 600/309; 600/316

(56) References Cited

U.S. PATENT DOCUMENTS

| | | | | |
|---|---|---|---|---|
| 7,782,192 | B2* | 8/2010 | Jeckelmann et al. | 340/539.12 |
| 2005/0143635 | A1 | 6/2005 | Kamath et al. | 600/347 |
| 2006/0224141 | A1* | 10/2006 | Rush et al. | 604/503 |
| 2006/0264835 | A1 | 11/2006 | Nielsen et al. | 604/174 |
| 2007/0021733 | A1 | 1/2007 | Hansen et al. | 604/890.1 |
| 2007/0066955 | A1 | 3/2007 | Sparholt et al. | 604/415 |
| 2008/0242962 | A1 | 10/2008 | Roesicke et al. | 600/347 |
| 2009/0028824 | A1* | 1/2009 | Chiang et al. | 424/85.7 |
| 2010/0100048 | A1 | 4/2010 | Nielsen et al. | 604/173 |
| 2010/0210928 | A1* | 8/2010 | Chou | 600/323 |
| 2011/0046548 | A1 | 2/2011 | Sakata et al. | 604/67 |
| 2011/0137255 | A1 | 6/2011 | Nielsen et al. | 604/173 |

OTHER PUBLICATIONS

International Search Report for PCT/JP2010/060895 (mailed Sep. 14, 2010).
User's Guide of Seven CGM System by DEXCOM.
User's Guide of Freestyle Navigator CGM System by Abbott.
Extended European Search Report issued in corresponding European Patent Application No. 10794085.0 dated Sep. 26, 2014.

* cited by examiner

CONTINUOUS ANALYSIS DEVICE AND SAMPLE COMPONENT CONTROL SYSTEM

CROSS-REFERENCE TO RELATED APPLICATIONS

This application is the U.S. National Phase under 35 U.S.C. §371 of International Application PCT/JP2010/060895, filed Jun. 25, 2010, which claims priority to JP Application No. 2009-156447, filed Jun. 30, 2009, which are hereby incorporated by reference in their entirety.

TECHNICAL FIELD

The present invention relates to a continuous analysis device (a continuous analysis apparatus) for analyzing a component in a sample using a sensor placed in a body, and a system for controlling a component in a sample using the continuous analysis apparatus.

PRIOR ART

As a method of controlling glucose concentration in blood, a method of using a continuous glucose monitoring apparatus along with an insulin dosing apparatus has been proposed.

The continuous glucose monitoring apparatus is an apparatus that measures, using a glucose sensor placed under skin of an abdominal region, an arm region or the like of a human body, glucose concentration in a body fluid such as blood, interstitial fluid, etc. on a continuous basis. The continuous glucose monitoring apparatus is used being fixed to the abdominal region or the arm region of the human body by an adhesive film.

On the other hand, the insulin dosing apparatus is an apparatus that doses insulin into a patient's body according to the glucose concentration measured by the continuous glucose monitoring apparatus. The insulin dosing apparatus is used being fixed to the human body directly or to the clothes of the user.

For transmitting data corresponding to the glucose concentration from the continuous glucose monitoring apparatus to the insulin dosing apparatus, a wire communication method using a cable, etc, or a radio communication method using an infrared ray or a radio wave of a 2.45-GHz frequency band is adopted (refer to, for example, patent documents 1-4).

PRIOR ART DOCUMENTS

Patent Documents

Patent document 1: U.S. Pat. No. 7,417,191
Patent document 2: Japanese National Publication of International Patent Application No. 2007-509661
Patent document 3: U.S. Patent Application No. 2005-0143635
Patent document 4: U.S. Pat. No. 6,175,752

BRIEF SUMMARY OF THE INVENTION

Problems to be Solved by the Invention

However, when a wire communication method is adopted as a communication method between the continuous glucose monitoring apparatus and the insulin dosing apparatus, the cable connecting the continuous glucose monitoring apparatus with the insulin dosing apparatus may touch a patient's skin, thereby giving the patient displeasure. Moreover, when the cable is caught in the patient's clothes, arm, etc. and is disconnected from the continuous glucose monitoring apparatus or the insulin dosing apparatus, communication will not be performed correctly.

On the other hand, when a radio communication method is adopted as the communication method, since the communication data between the continuous glucose monitoring apparatus and the insulin dosing apparatus gets entangled with the communication data of other communication facilities, such as a cellular phone, a possibility that data does not correctly transmitted to the insulin dosing apparatus becomes high. In such a case, wrong amount of insulin is injected from the insulin dosing apparatus to the patient's body. Consequently, control of the insulin level by the whole insulin level control system may not be done correctly.

An object of the present invention is to provide a technique capable of transmitting information about components in body fluid measured by a continuous analysis apparatus to another apparatus more correctly without giving user displeasure.

Means for Solving the Problems

A continuous analysis apparatus according to the present invention includes: a sensing unit including a sensor that is held in subcutaneous tissue for obtaining information with respect to an objective substance in a sample; and a data holding unit having a storage means for storing the information obtained from the sensor or data corresponding to the information. Further, the sensing unit and the data holding unit of the continuous analysis apparatus are configured so as to be separably joined to each other.

Note that, the "sample" herein implies body fluid such as blood, intercellular fluid and the like. The "objective substance" implies glucose, lactic acid, or cholesterol contained in body fluid such as blood and intercellular fluid. The "information obtained from the sensor" implies current value output from the sensor and value which is obtained by converting the current value output by the sensor into the voltage value. Moreover, the "data corresponding to the information obtained from a sensor" implies the quantity or concentration of the objective substance calculated based on the current value output from the sensor (or value which is obtained by converting the current value output by the sensor into the voltage value).

The sensing unit and the data holding unit may have their respective engaging means for separably joining the data holding unit to the sensing unit.

The sensing unit and the data holding unit may have their respective data communication units for enabling data transmission from the sensing unit to the data holding unit or from the data holding unit to the sensing unit.

Note that, data transmitted from the sensing unit to the data holding unit is, for example, the current value output by the sensor (or value which is obtained by converting the current value output by the sensor into the voltage value), quantity or concentration data calculated based on the current value output by the sensor (or value which is obtained by converting the current value output by the sensor into the voltage value). Moreover, data transmitted from the data holding unit to the sensing unit is, for example, data for revising (or updating) the program or data that the sensing part uses to perform various operations.

The data communication units may be the units enable the data transmission in a condition where the sensing unit and the data holding unit do not come in contact with each other. Moreover, the data communication units may have their respective connector units, the connector units enabling the data transmission when the sensing unit and the data holding unit come in contact with each other.

Each connector unit may be placed in one engaging means. In that case, the data transmission between the sensing unit and the data holding unit is enabled by joining the data holding unit with the sensing unit.

Each engaging means may be placed in one connector unit. In this case, the data holding unit can be joined to the sensing unit by bringing the data holding unit and the external apparatus into contact.

Note that, the present invention can be grasped as a sample component control system equipped with the continuous glucose monitoring apparatus and an external apparatus. For example, the present invention is a sample component control system including the above continuous analysis apparatus and an external apparatus, the external apparatus has a storage means for storing the information obtained from the sensor or data corresponding to the information stored in the storage means of the data holding unit, and the data holding unit and the external apparatus are separably joined together.

In the above sample component control system, the sensing unit and the data holding unit may have their respective engaging means for separably joining the data holding unit to the sensing unit.

In the above sample component control system, the external apparatus and the data holding unit may have their respective data communication unit for enabling data transmission from the external apparatus to the data holding unit or from the data holding unit to the external apparatus.

Note that, data transmitted from the external apparatus to the data holding unit is, for example, data for revising (or updating) the program or data that the sensing part uses to perform various operations. Moreover, data transmitted from the data holding unit to the external unit is, for example, the current value output by the sensor (or value which is obtained by converting the current value output by the sensor into the voltage value), quantity or concentration data calculated based on the current value output by the sensor (or value which is obtained by converting the current value output by the sensor into the voltage value).

The data communication units may be units that enable the data transmission in a condition where the external unit and the data holding unit do not come in contact with each other. Moreover, the data communication units may have their respective connector units, the connector units enabling the data transmission when the sensing unit and the data holding unit come in contact with each other.

Each connector unit may be placed in one engaging means. In this case, the data transmission is enabled by joining the data holding unit to the external apparatus. Each engaging means may be placed in one engaging means. In this case, the data holding unit can be joined to the external apparatus by bringing the data holding unit and the external apparatus into contact.

Note that, in the sample component control system, the external apparatus may be a medicine dosing apparatus for dosing medicine into a body, an information processing apparatus for managing information related to a sample component, or a display unit for displaying concentration of a sample component.

The display unit may be a unit that displays information obtained by the sensor of the continuous analysis apparatus or the data corresponding to the information. The display unit may be a unit that measures concentration of an objective component in a sample extracted from the body. Further, the display may be a unit that converts information obtained by the sensor of the continuous analysis apparatus into data corresponding to the information based on the concentration of the objective component in the sample extracted from the body.

The medicine dosing apparatus may be an apparatus that inject of a certain quantity to the body based on the data corresponding to the information obtained by the sensor of the continuous glucose monitoring apparatus.

The sensor may be a glucose sensor, for example. Of course, the sensor may be a sensor that measures lactic acid and cholesterol.

Advantages of the Invention

According to the present invention, information about components in the body fluid measured by the continuous analysis apparatus can be transmitted to another apparatus more correctly without giving a user displeasure.

BRIEF EXPLANATION OF THE DRAWINGS

FIG. 1(a) is a whole perspective diagram showing an example of the continuous glucose monitoring apparatus according to the present invention, and FIG. 1 (b) is a whole perspective diagram showing the continuous glucose monitoring apparatus shown in FIG. 1 (a) which is in a state where the data holding unit is separated.

FIG. 5 (a) and FIG. 5 (b) are enlarged sectional diagrams showing the connector units in the continuous glucose monitoring apparatus shown in FIG. 1 (a) and FIG. 1 (b).

EMBODIMENT(S) OF THE INVENTION

Embodiments of the present invention will hereinafter be described with reference to the accompanying drawings.

First, a continuous glucose monitoring apparatus, which is an example of the continuous analysis apparatus according to the present invention, will be discussed with reference to FIGS. 1-6.

Figure 1:
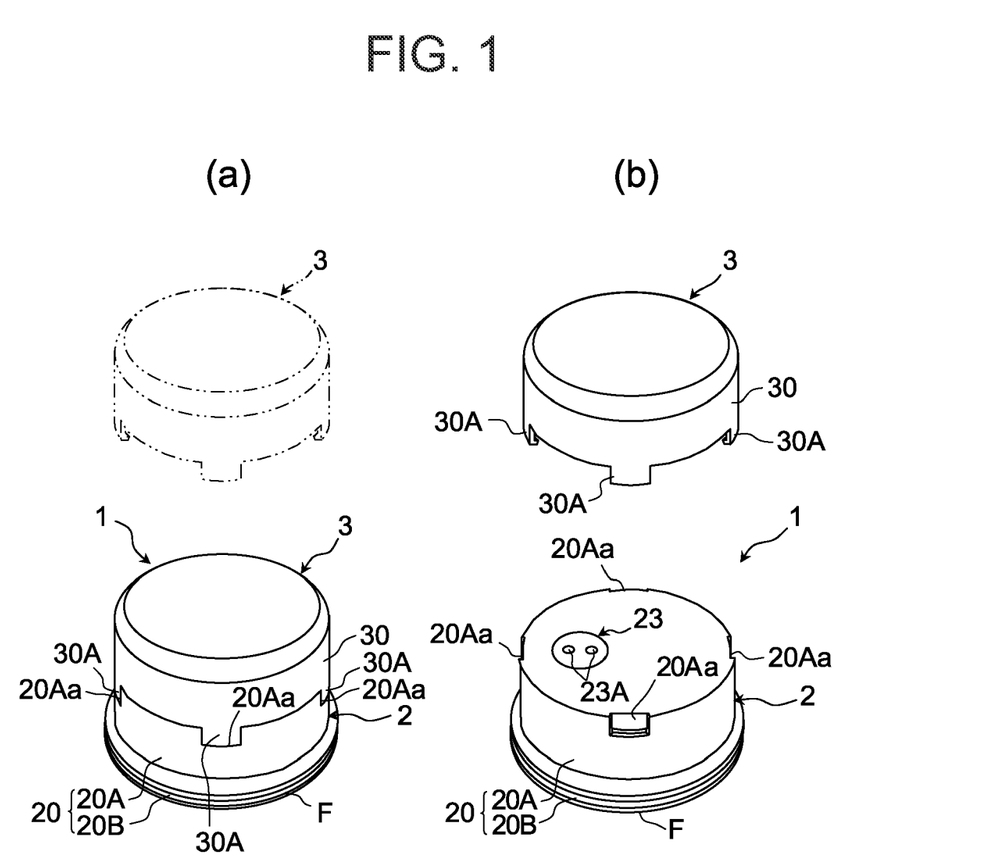
Figure 2:
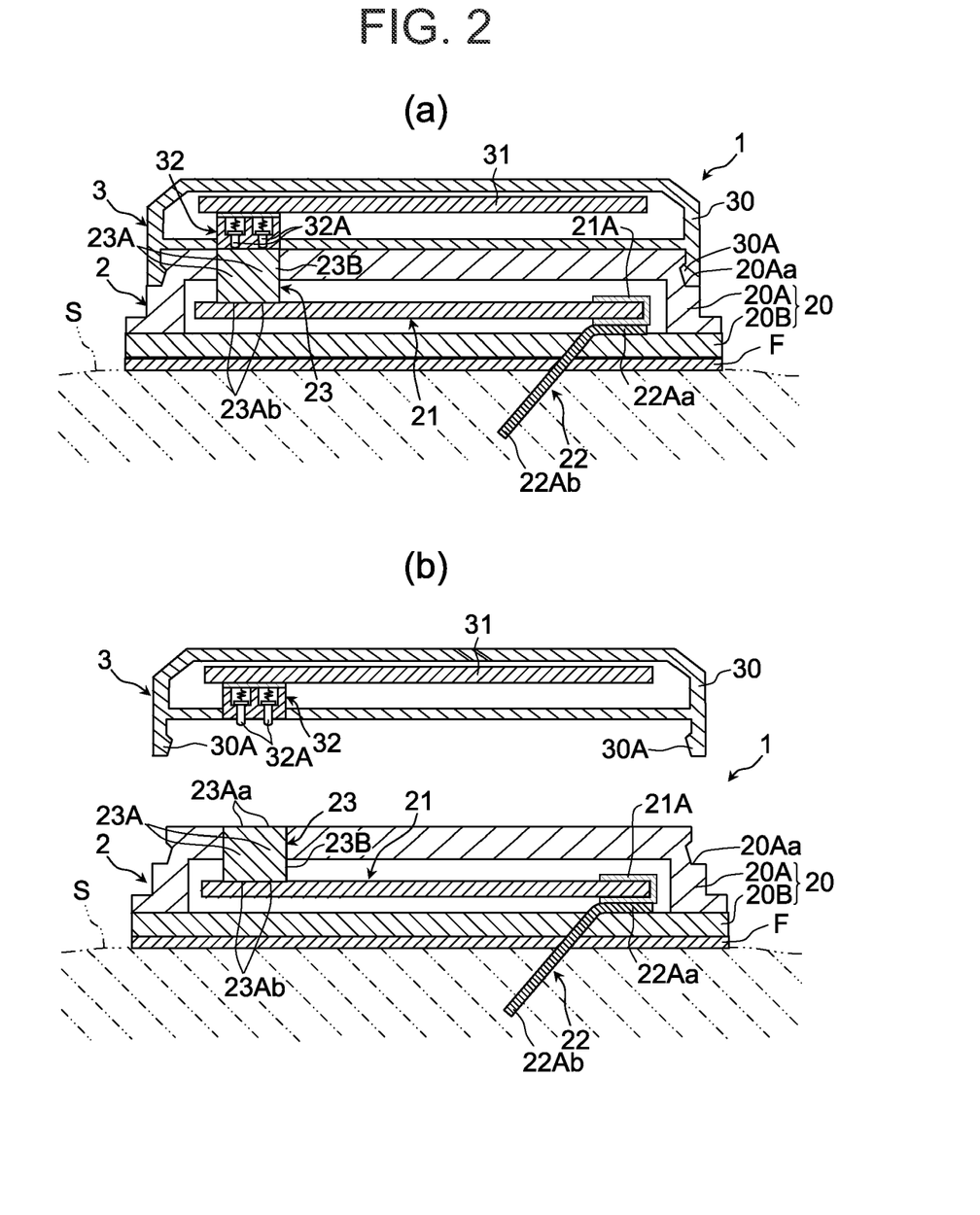
FIG. 2 is a sectional diagram of the continuous glucose monitoring apparatus shown in FIG. 1 (a), and FIG. 2 (b) is a whole perspective diagram showing the continuous glucose monitoring apparatus, shown in FIG. 2 (a), in a state where the data holding unit is separated.
Figure 3:
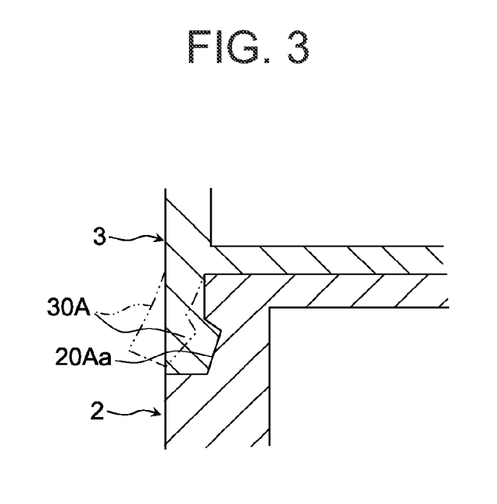
FIG. 3 is an enlarged sectional diagram showing principal parts (circumference of a hook and a concave part) of the continuous glucose monitoring apparatus shown in FIG. 1 (a).

The continuous glucose monitoring apparatus 1 shown in FIGS. 1 and 2 is an apparatus that can measure continuously glucose concentration in a body fluid, such as blood and intercellular fluid, and that is used being attached to a part of a human body, such as the skin S of the shoulder or the abdomen region. This continuous glucose monitoring apparatus 1 is provided with a sensing unit 2 and a data holding unit 3.

As shown in FIG. 2 (a) and FIG. 2 (b), the sensing unit 2 is a unit that is fixed to the skin S, and it is provided with a case 20, a circuit board 21, a glucose sensor 22, and a connector unit 23.

The case 20 is a part that makes the outside of the continuous glucose monitoring apparatus 1, and it includes a cover 20A and a substrate 20B. As for the case 20, it is desirable to have waterproofness or water resistance. The cover 20A (and the substrate 20B, if necessary) of the case 20 is formed, for example, from material with a very low permeability, such as metal, polypropylene resin, etc.

The cover 20A is a part that accommodates the circuit board 21 in the space demarcated by itself and the substrate 20B, and it is formed to have a cylindrical shape. This cover 20A has one or more (three in the figure) concave parts 20Aa that serve as an engaging means. As shown in FIG. 2 (a) and FIG. 3, each concave part 20Aa is a part with which the hook 30A of the data holding unit 3, which will be described later, engages. The shape of the concave part 20Aa is not limited to the illustrated shape. Any shape is available, so long as it can engage the hook 30A so that the data holding unit 3 is fixed to the sensing unit 2.

As shown in FIG. 2 (a) and FIG. 2 (b), the substrate 20B is a member into which the glucose sensor 22 is inserted and to which the end part 22Aa of the glucose sensor 22 is fixed. To the substrate 20B, an adhesive film F is fixed. This adhesive film F is a member that is used for fixing the continuous glucose monitoring apparatus 1 to the skin. As the adhesive film F, the tape both sides of which has adhesiveness may be used.

The circuit board 21 is a unit that is provided with electronic components required for predetermined operations (for example, applying voltage, calculation of glucose concentration, and communication with the exterior) of the continuous glucose monitoring apparatus 1. This circuit board 21 is provided with a terminal 21A for establishing electrical contact with the electrode 22B (refer to FIG. 4) of the glucose sensor 22 which will be described later. This terminal 21A is used for applying voltage to the glucose sensor 22 and obtaining response current value from the glucose sensor 22.

Figure 4:
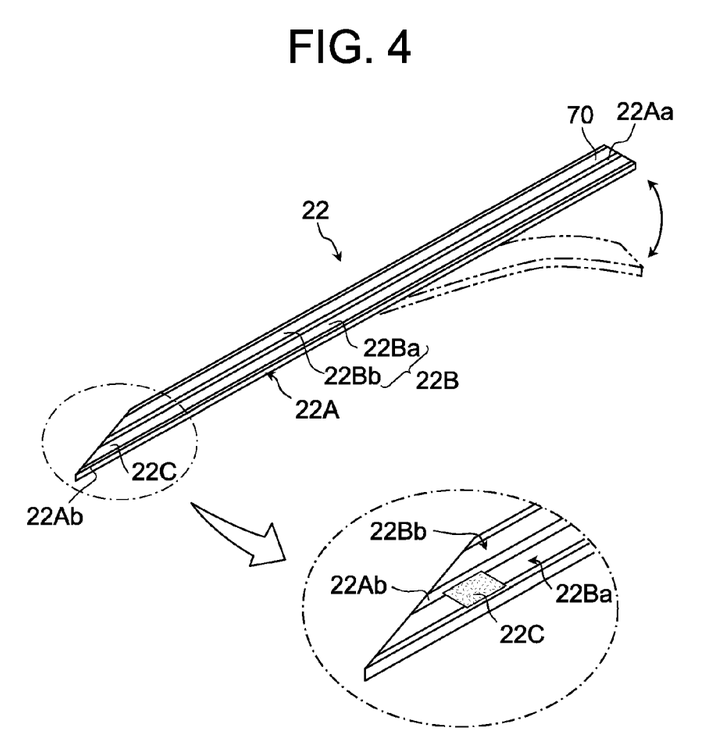
FIG. 4 is a whole perspective diagram showing the glucose sensor in the continuous glucose monitoring apparatus shown in FIG. 3 together with an enlarged diagram of principal parts.

As shown in FIG. 2 and FIG. 4, the glucose sensor 22 is a sensor for obtaining information (response current value) according to the glucose concentration in the body fluid such as blood and intercellular fluid. The end part 22Aa of this glucose sensor 22 projects from the skin S and contacts with the terminal 21A of the circuit board 21, and the greater part of the remainder part is buried in the skin S.

Of course, the glucose sensor 22 may be the one that is completely buried in a subcutaneous tissue. Note that, in this case, applying voltage to the glucose sensor 22 and obtaining response current value from the glucose sensor 22 can be performed through leads prepared so as to connect the glucose sensor 22 and the terminal on the circuit board 21.

As shown in FIG. 4, the glucose sensor 22 has a substrate 22A, electrodes 22B, and the immobilized enzyme part 22C.

The substrate 22A is a sheet-like member for supporting the electrodes 22B, and it has insulating property and flexibility. The substrate 22A is formed so as to have the end part 22Ab with a sharp shape and the end part 22Aa that is to be placed within the case 20. The sharp-shaped end part 22Ab allows sticking the glucose sensor 22 in the skin S easily, thereby reducing a user's pain. Note that, the shape of the end part 22Aa and the method of burying the end part 22Aa under the skin is not limited to the above-mentioned shape and method. For example, a method including: forming the end part 22Aa to have a cylindrical shape; arranging an insertion needle in the end part 22Aa; sticking the end part 22A to the skin utilizing the insertion needle; and then removing the insertion needle can be used. A method including: forming the end part 22Aa to have a cylindrical shape; arranging the end part 22Aa in an insertion needle; sticking the end part 22A to the skin utilizing the insertion needle; and then removing the insertion needle can be also used.

As a material for forming the substrate 22A, any material can be used, so long as it is harmless to human bodies and has suitable insulation property, and therefore, for example, a thermoplastic resin such as PET, PP and PE, a polyimide resin or an epoxy resin can be used.

The electrodes 22B are electrodes that are used for applying voltage to the immobilized enzyme part 22C and for taking out electrons from the immobilized enzyme part 22C. The electrode 22B includes a working electrode 22Ba and a counter electrode 22Bb. The working electrode 22Ba is an electrode for performing electronic transfer from/to glucose. The counter electrode 22Bb is an electrode used for applying voltage together with the working electrode 22Ba. The electrode 22B can be formed by the screen printing of a carbon ink.

The immobilized enzyme part 22C is a part that mediates the electronic transfer between glucose and the working electrode 22Ba. This immobilized enzyme unit 22C is formed by immobilizing glucose redox enzyme in the end of the working electrode 22Ba.

As the glucose redox enzyme, glucose oxidase (GOD) or glucose dehydrogenase (GDH) can be used. As the method of immobilizing glucose redox enzyme, any one of well-known various methods, for example, the method that utilizes polymerizable gel, macromolecule such as polyacrylamide etc., MPC polymer that is phospholipid polymer with silane coupling agent, or protein film, can be adopted.

Figure 5:
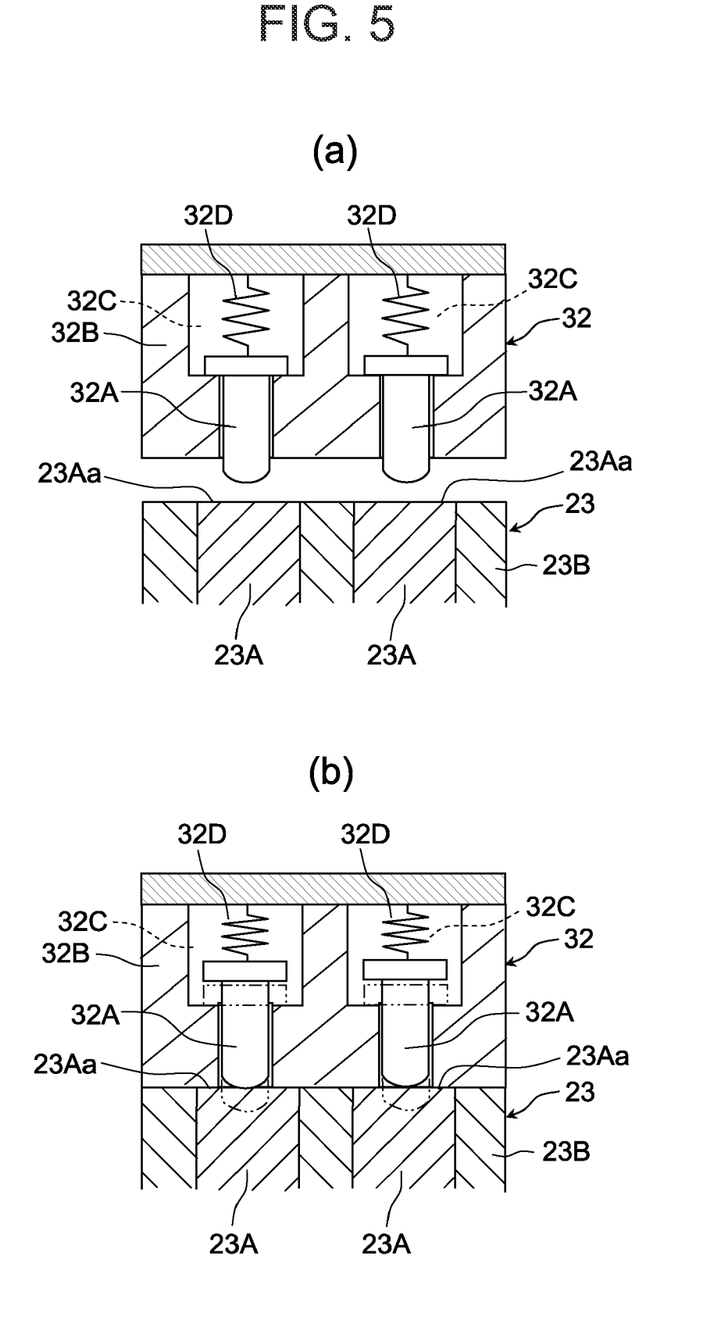

As shown in FIG. 2 and FIG. 5, the connector unit 23 is a unit for transporting information (response current value) stored in a data storage unit 25 after-mentioned (refer to FIG. 6) to a data storage unit 34 after-mentioned (refer to FIG. 6) of the data holding unit 3, and it has pillar-shaped terminals 23A and a holder 23B. The pillar-shaped terminal 23A has contact parts 23Aa and 23Ab. The contact part 23Aa is a part that is electrically contacted with the pin-like terminal 32A of the connector unit 32 in the data holding unit 3 which will be described later. The contact part 23Ab is a part that is electrically contacted with the circuit board 21. The pillar-shaped terminal 23A can be formed by insert molding with the pillar-shaped member formed from a material having high conductivity, such as metal material, carbon material, etc. when resin molding of the holder 23B is performed.

Figure 6:
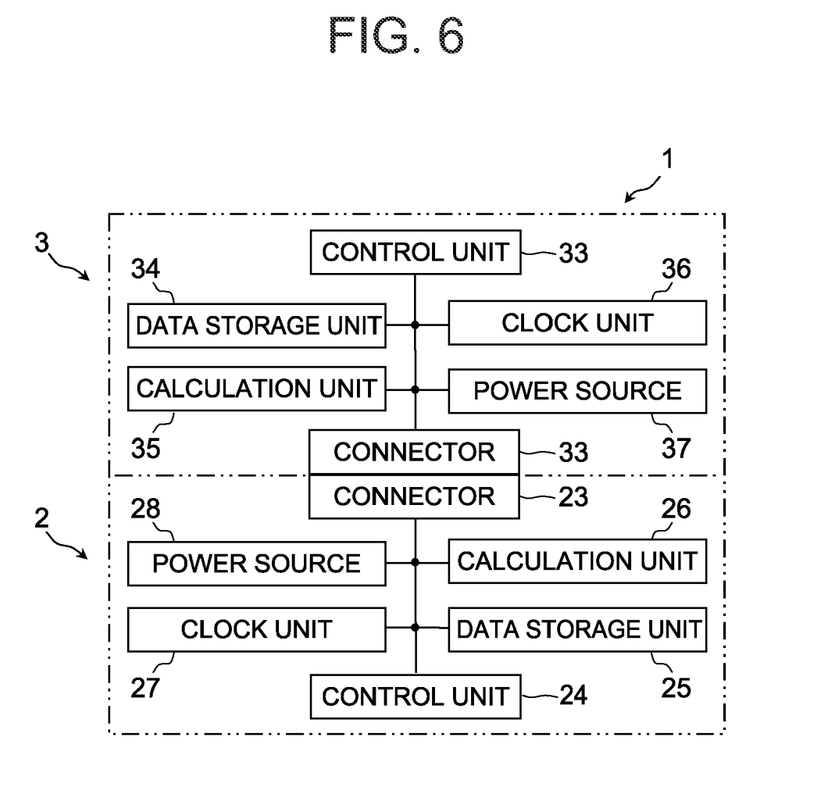
FIG. 6 is a block diagram showing schematic configuration of the continuous glucose monitoring apparatus shown in FIG. 1 (a).

The sensing unit 2 is provided with, other than the circuit board 21, the glucose sensor 22 and the connector unit 23, a control unit 24, a data storage unit 25, a calculation unit 26, a clock unit 27, and a power supply 28 as shown in FIG. 6. The control unit 24, the data storage unit 25, the calculation unit 26 and the clock unit 27 are actualized by the electronic components, for example, CPU (or MPU), ROM and RAM in the circuit board 21.

The control unit 24 is a unit for controlling various kinds of operations in the sensing unit 2, for example, timing of applying voltage to the glucose sensor 22, an value of applied voltage, sampling of response current, and communication with the data holding unit 3.

The data storage unit 25 stores a program and data (for example, data about a voltage applying pattern) required for various kinds of operations in the sensing unit 2.

The data storage unit 25 stores response current value obtained by the glucose sensor 22 in addition to the above-mentioned program and data. Note that, a "response current value" herein implies a value obtained by converting the response current value into voltage.

Moreover, the data storage unit 25 may store data about a calibration curve, compensation data, and data (for example, glucose concentration in the body fluid, such as blood or intercellular fluid, calculated based on the data about the response current value and the calibration curve) corresponding to the response current value from the glucose sensor 22.

The calculation unit 26 calculates the glucose concentration in the body fluid, such as blood or intercellular fluid, based on the information such as the response current value etc. and the calibration curve data stored in the data storage unit 25. It is possible to configure the calculation unit 26 so as to calculate glucose concentration in the body fluid, such as blood or intercellular fluid, using the calibration curve data corresponding to the temperature of the body fluid, such as blood or intercellular fluid. When calculation of the glucose concentration in the body fluid, such as blood or intercellular fluid, is performed in a data holding unit 3 which will be described later, the calculation unit 26 can be omitted.

The clock unit 27 is a unit for measuring a time at which predetermined operation is performed, or a period of time elapsed from a time when predetermined operation is started. For example, the clock unit 27 measures a time at which response current is sampled, a time at which the data holding unit 3 is separated from the sensing unit 2, a period of time elapsed from a time when the data holding unit 3 is separated from the sensing unit 2, a period of time elapsed from a time when the glucose sensor 22 is exchanged, etc. These pieces of time information may be stored in the data storage unit 25 as information associated with the glucose concentration calculated by the calculation unit 26 and the response current value from the glucose sensor 22.

The power supply 28 is a direct-current power supply for supplying electric power to the circuit board 21 and the glucose sensor 22. As the power supply 28, for example, the button cell whose power supply voltage is 1-3V is used.

The data holding unit 3 is a unit for migrating, to an external apparatus of the continuous glucose monitoring apparatus 1, at least one of information (response current value from the glucose sensor 22) stored in the data storage unit 25 of the sensing unit 2, data corresponding to the information (glucose concentration etc. which the calculation unit 26 calculated based on the response current value from the glucose sensor 22 and data related to the calibration curve), and the above-mentioned time information. As examples of the external apparatus herein, an insulin dosing apparatus, a self-monitoring blood glucose apparatus that uses a disposable sensor, and a personal computer can be mentioned. This data holding unit 3, as shown in FIG. 1 and FIG. 2, can be attached to or detached from the sensing unit 2, and it is provided with a case 30, a circuit board 31, and a connector unit 32.

The case 30 is a member that makes the outside of the data holding unit 3, and it is formed so as to have a cylindrical shape as a whole. It is desirable that the case 30 has water-proofness or water resistance. The case 30 is formed from, for example, a material with very low permeability, such as metal, polypropylene resin, etc.

The case 30 has one or more (three in the figure) hooks 30A that serve as an engaging means. Each hook 30A is a part that engages with the concave part 20Aa of the case 20 (cover 20A) in the sensing unit 2. The hook 30A of the case 30 is projected downward and has elasticity. That is, the data holding unit 3 is fixed to the sensing unit 2 by engaging the hooks 30A of the case 30 in the data holding unit 3 with the concave parts 20Aa of the case 20 in the sensing unit 2. Moreover, the data holding unit 3 can be removed from the sensing unit 2 by releasing the engagement between the hooks 30A and the concave parts 20Aa.

Here, in case of forming two or more hooks 30A, it is preferable that one hook 30 A is formed so as to have a different shape from the other hooks 30 in order to be able to joining the data holding unit 3 to the sensing unit 3 without adjusting the direction of the data holding unit. Moreover, it is possible to mark a symbol on the concave part 20Aa or the hook 30A, or near the concave part 20Aa or the hook 30A in order to be able to joining the data holding unit 3 to the sensing unit 3 without adjusting the direction of the data holding unit.

The circuit board 31 is provided with electronic components required for predetermined operations of the data holding unit 3, and it is electrically connected to the connector unit 32. More specifically, the circuit board 31 is provided with the electronic parts for constructing the control unit 33, the calculation unit 35, the data storage unit 34 and the clock unit 36 as shown in FIG. 6. The circuit board 31 is further configured so that electric power is supplied from the power supply 37.

The control unit 33 is a unit that controls various kinds of operations of the data holding unit 3, for example, transmission of data to the data holding unit 3, and transmission of data to another information processing apparatus.

The calculation unit 35, the data storage unit 34, the clock unit 36, and the power supply 37 have the same function as the data storage unit 25, the calculation unit 26, the clock unit 27 and the power supply 28 in the sensing unit 2, respectively.

However, when the calculation unit 26 and the clock unit 27 are provided in the sensing unit 2, the calculation unit 35 and the clock unit 36 in the data holding unit 3 can be omitted, and when the calculation unit 35 and the clock unit 36 are provided in the data holding unit 3, the calculation unit 26 and the clock unit 27 in the sensing unit 2 can be omitted. Moreover, when the power supply 37 is provided in the data holding unit 3, the power supply 28 in the sensing unit 2 can also be omitted, and when the power supply 28 is provided in the sensing unit 2, the power supply 37 in the data holding unit 3 can be omitted. Note that, in the continuous glucose monitoring apparatus 1 in which the power supply 37 is provided only in the data holding unit 3, when the data holding unit 3 is separated from the sensing unit 2, measurement of glucose concentration is stopped because power supply from the data storage unit 3 to the sensing unit 2 is stopped. Consequently, it is possible to lengthen the life of the glucose sensor 22. Moreover, when the power supply 28 in the sensing unit 2 is omitted, the sensing unit 2 can be made more compact, and it is therefore possible to lessen a feeling of wrongness invoked by the sensing unit 2 fixed to the patient's body. Furthermore, when adopting the configuration where the power supply 37, the calculation unit 35 and the clock unit in the data holding unit 3 are omitted, it becomes possible to use a small storage medium (for example, a flash memory such as an SD memory card, SmartMedia (registered trademark), etc.) as the data holding unit 3.

Moreover, when the calculation unit 26 is provided in the sensing unit 2, it is not necessary to store the calibration curve data and the temperature correction data in the data storage unit 34 of the data holding unit 3, and when the calculation unit 35 is provided in the data holding unit 3, it is not necessary to store the calibration curvet data and the temperature correction data in the data storage unit 25 of the sensing unit 2. Note that, when providing the data storage unit 34 in the data holding unit 3, it is also possible to omit the data storage unit 25 in the sensing unit 2.

The connector unit 32 is a unit for transmitting information (response current value) from the data storage unit 25 in the sensing unit 2 to the data storage unit 34 in the data holding unit 3, and it has pin-like terminals 32A and a holder 32B as shown in FIG. 2 and FIG. 5. The pin-like terminal 32A is a part that is electrically contacted with the pillar-shaped terminal 23A (contact part 23Aa) of the connector unit 23 in the sensing unit 2. This pin-like terminal 32A is relatively movable against the holder 32B and is biased downward. The holder 32B is a member that holds the pin-like terminal 32A in a manner that permits movement of the pin-like terminal 32A. In the holder 32B, a space 32C is formed for permitting movement of the pin-like terminal 32A. Elastic members 32D, other than the pin-like terminals 32A, are provided in this space 32C. The elastic member 32D is a member for biasing the pin-like terminal 32A. Although coiled spring is illustrated as the elastic member 32D, the elastic member 32D may be a member other than the coiled spring, for example, a blade spring, resin materials such as rubber, etc.

In the continuous apparatus, when the data holding unit 3 is joined to the sensing unit 2, the pillar-shaped terminals 23A of the connector unit 23 in the sensing unit 2 and the pin-like terminals 32A of the connector unit 32 in the data holding unit 3 are electrically connected to each other. Therefore, the information (response current value) or the data (glucose concentration calculated from the response current value) corresponding to the information stored in the data storage unit 25 of the sensing unit 2 is transmitted to the data storage unit 34 of the data holding unit 3 through the connector units 23 and 32. Note that, the time information measured by the clock unit 27 (the time at which response current is sampled, the time at which the data holding unit 3 is separated from the sensing unit 2, the period of time elapsed from the time when the data holding unit 3 is separated from the sensing unit 2, the period of time elapsed from the time when the glucose sensor 22 is exchanged, etc.) is stored in the data storage unit 25, the time information may also be transmitted to the data storage unit 34 through the connectors 23 and 32.

On the other hand, the data holding unit 3 of the continuous glucose monitoring apparatus 1 can be separated from the sensing unit 2. Therefore, it is possible, by utilizing the data holding unit 3, to transport one of the information, the data corresponding to the information, and the time information that are stored in the data storage unit 25 of the sensing unit 2 to an information processing apparatus other than the continuous glucose monitoring apparatus 1.

Note that, when adopting the configuration in which the data storage unit 25 in the sensing unit 25 is omitted, the information (response current value) output from the glucose sensor 22 and/or the time information measured by the clock unit 27 (the time at which response current is sampled, the time at which the data holding unit 3 is separated from the sensing unit 2, the period of time elapsed from the time when the data holding unit 3 is separated from the sensing unit 2, the period of time elapsed from the time when the glucose sensor 22 is exchanged, etc.) are/is directly transmitted to the data storage unit 34 through the connectors 23 and 32. Moreover, it is possible to configure the sensing unit 2 and the data holding unit 3 so that the data transmission between them is performed wirelessly by using non-contact type IC cards such as FeliCa® instead of the connector units 23 and 32.

The continuous glucose monitoring apparatus according to the present invention is not limited to the examples discussed above, and may be modified in a variety of forms. For example, it is not necessarily that means for engaging the data holding unit 3 with the sensing unit 2 is means for engaging the hooks 30A of the data holding unit 3 with the concave parts 20Aa of the sensing unit 2. For example, means for engaging the data holding unit 3 with the sensing unit 2 may be means for engaging hook(s) of the sensing unit 2 with concave part(s) of the data holding unit 3. The means can be actualized by configuring the sensing unit 2 and the data holding unit 3 so that one of them fits in the other.

Figure 7:
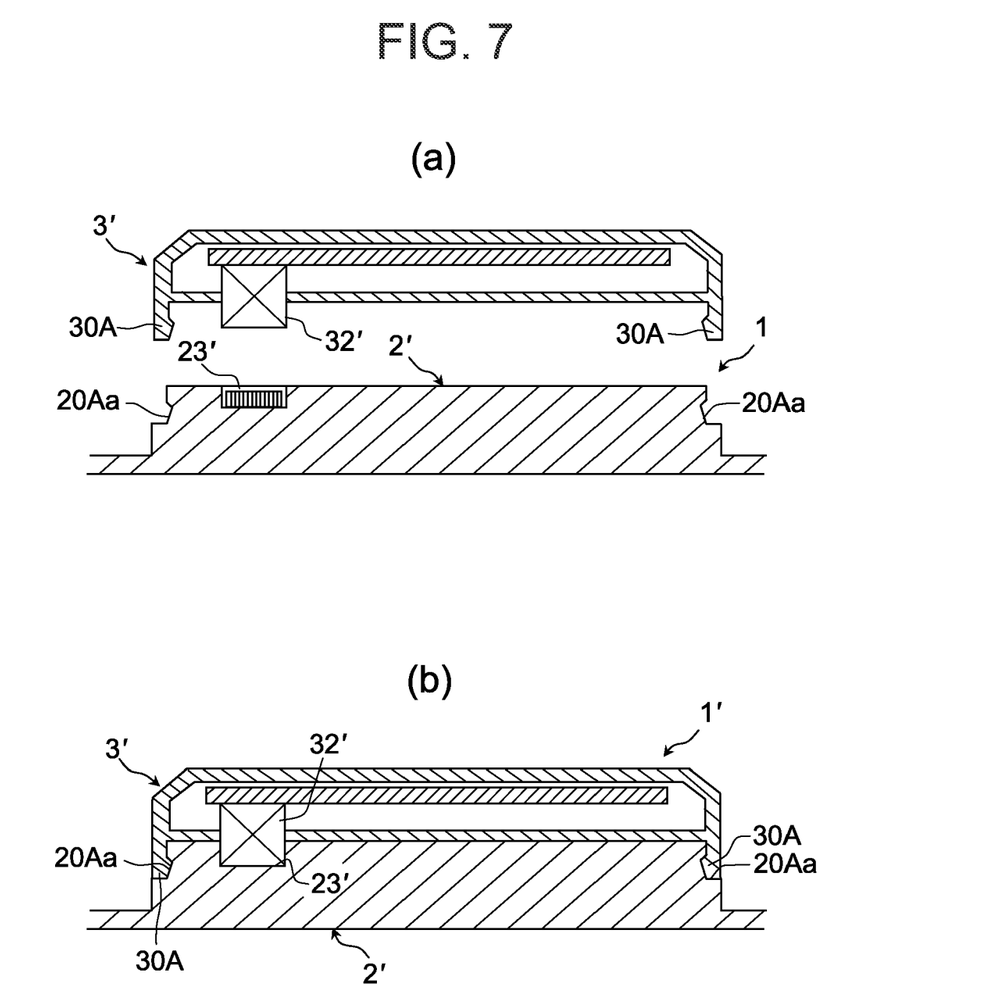
FIG. 7 is a sectional diagram showing another example of the connector units.
Figure 8:
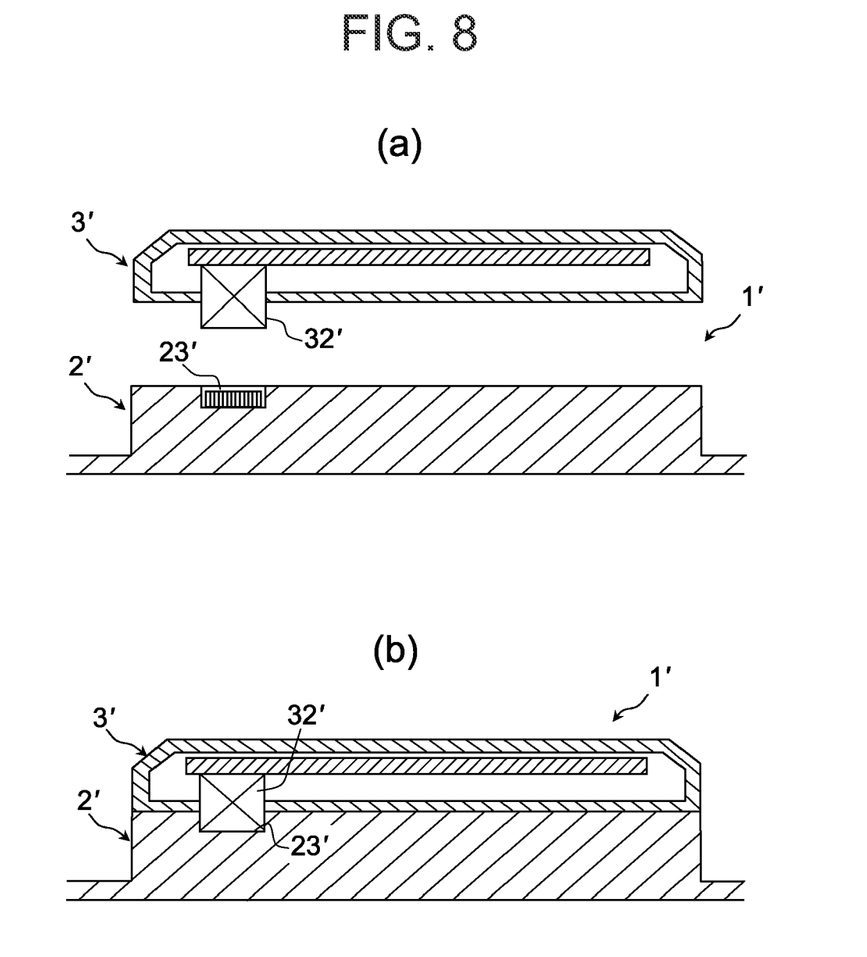
FIG. 8 is a sectional diagram showing still another example of the connector units and the engaging means.

Moreover, as shown in FIG. 7, the continuous glucose monitoring apparatus 1' may be the one that has a sensing unit 2' including a connector unit 23' with a convex shape and a data holding unit 3' including a connector unit 32' with a concave shape. That is, in this apparatus, by inserting the connector unit 32' into the connector unit 23', transmission of the data stored in the data storage unit 25 of the sensing unit 2' to the data holding unit 3' is enabled. With this configuration, data migration from the data holding unit 3' to another information processing apparatus can be performed using the connector unit (for example, the connector unit for USB) provided in the information processing apparatus. Moreover, as shown in FIG. 8, the concave parts 20Aa and the hooks 30A that serve as the engaging means may be omitted, and the connector units 23' and 32' that function as an engaging means may be used. Of course, in the continuous glucose monitoring apparatus 1, the connector unit 23' may be the one with a concave shape, and the connector unit 32' may be the one with a convex shape.

Figure 9:
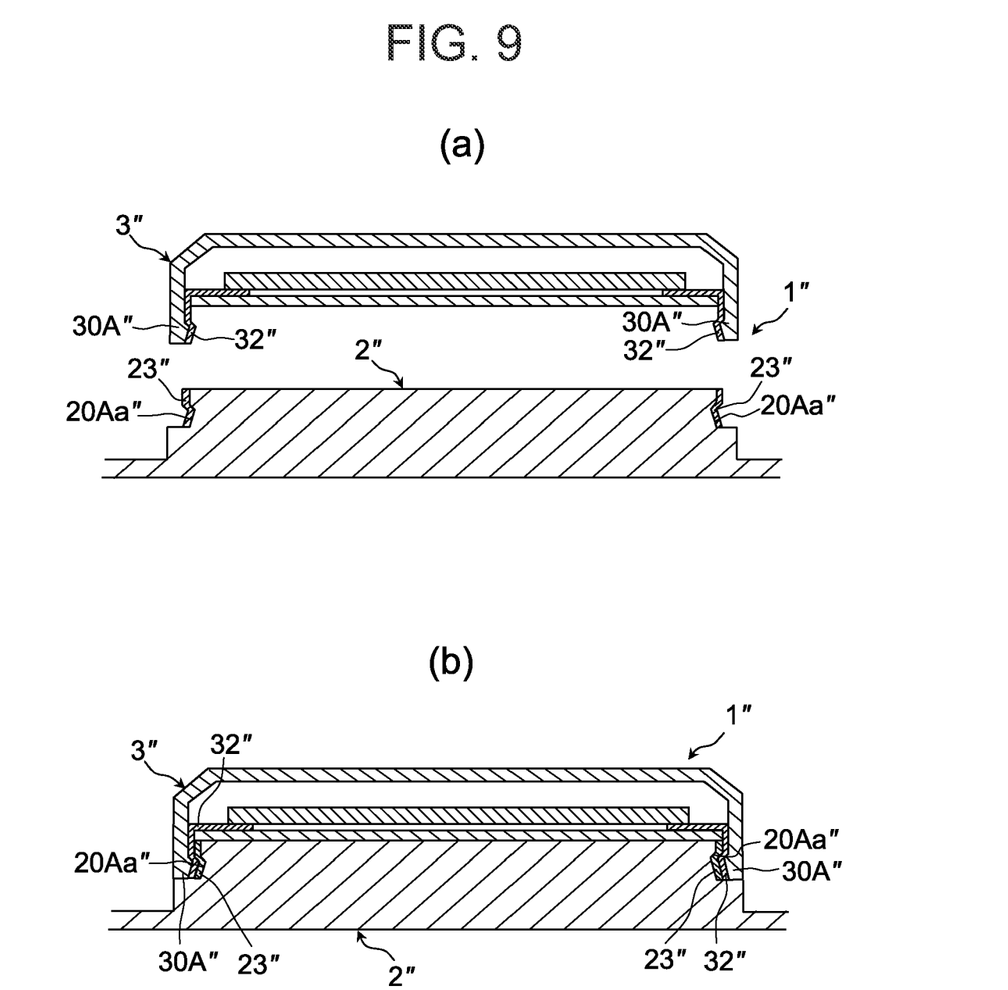
FIG. 9 is a sectional diagram showing yet another example of the connector units and the engaging means.

The continuous insulin measuring apparatus 1" shown in FIG. 9 is an apparatus that has the engaging means provided with the connector unit. That is, the continuous glucose monitoring apparatus 1" is provided with conductor parts that serve as the connector unit 23 "and 32" formed on the surfaces of hooks 30A" of the data holding unit 3" and on the surfaces of the concave parts 20Aa of the sensing unit 2".

Next, a insulin level control system, which is an example of the body fluid control system according to the present invention, will be discussed with reference to FIG. 10 and FIG. 11.

Figure 10:
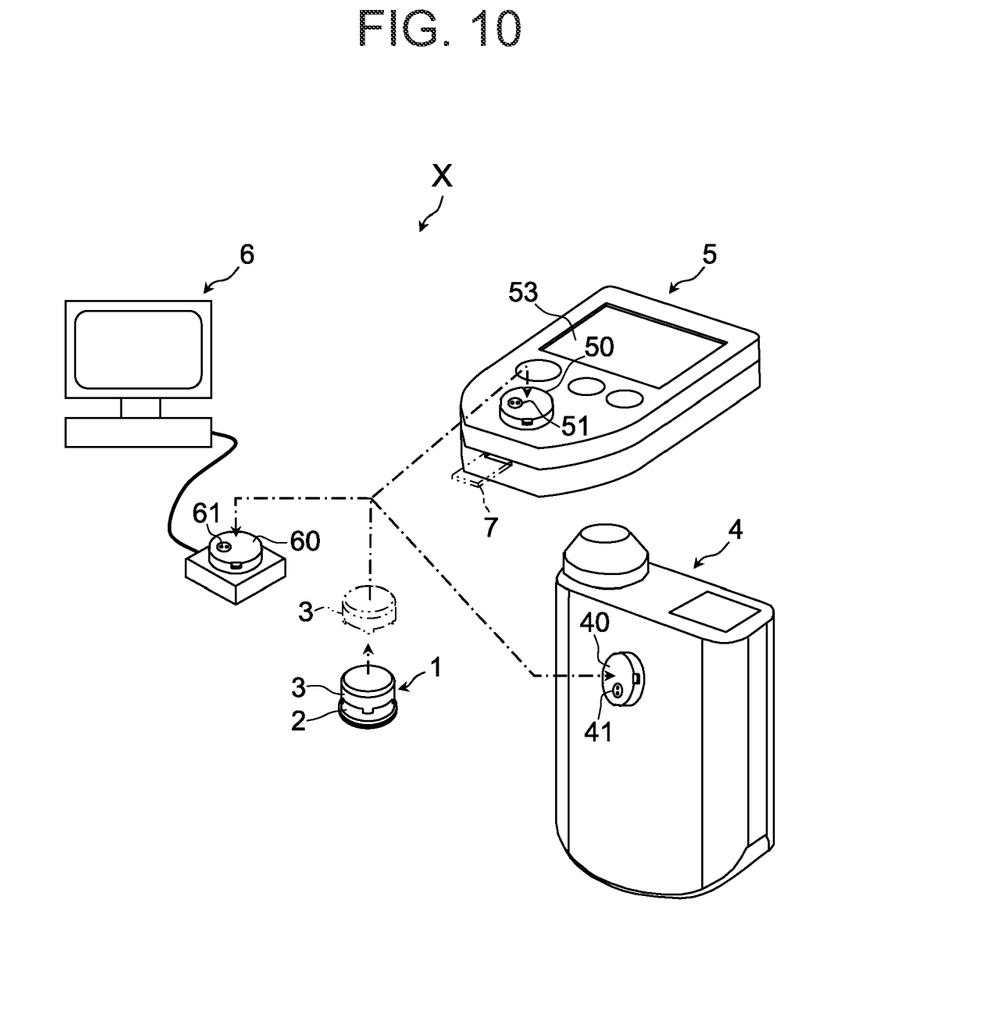
FIG. 10 is a whole perspective diagram showing an example of the insulin level control system of the present invention.

The insulin level control system X shown in FIG. 10 includes the continuous glucose monitoring apparatus 1 and external apparatuses 4, 5, and 6. Note that, the external apparatus 4 in FIG. 10 is the insulin dosing apparatus. The external apparatus 5 in FIG. 10 is the self-monitoring blood glucose apparatus. The external apparatus 6 in FIG. 10 is the information processing apparatus 6.

The continuous glucose monitoring apparatus 1 is the apparatus previously described with reference to FIG. 1 through FIG. 6, and has the sensing unit 2 and the data holding unit 3. The sensing unit 2 and the data holding unit 3 have the connector units 23 and 32. The data holding unit 3 is provided with the hooks 30A for separably joining the data holding unit 3 to the sensing unit 2, and the data storage unit 34 for storing the information (response current value or data corresponding to the value (glucose concentration calculated from response current value)) obtained from the glucose sensor 22, the time information (the time at which response current is sampled, the time at which the data holding unit 3 is separated from the sensing unit 2, the period of time elapsed from the time when the data holding unit 3 is separated from the sensing unit 2, the period of time elapsed from the time when the glucose sensor 22 is exchanged, etc.) measured by the clock unit 27 (or the clock unit 36), etc.

Figure 11:
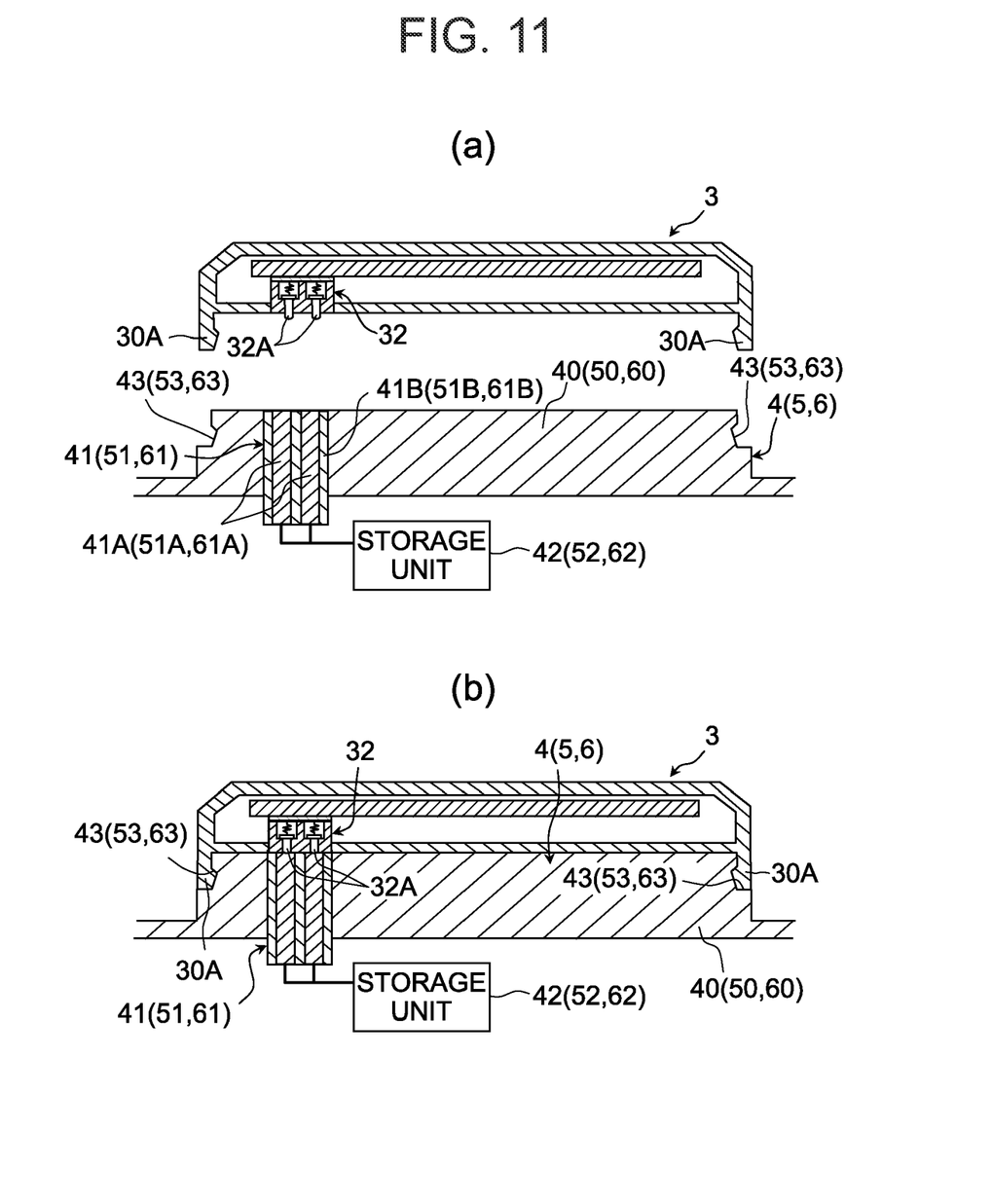
FIG. 11 is a sectional diagram showing relationship between the data holding unit of the continuous glucose monitoring apparatus shown in FIG. 1 (a), and fixing part and connector unit of the insulin dosing apparatus, a self-monitoring blood glucose apparatus, and an information processing apparatus.

As shown in FIG. 10 and FIG. 11, the insulin dosing apparatus 4 is for injecting an insulin into the body, and has a holding part 40, a connector unit 41, and a storage unit 42.

The self-monitoring blood glucose apparatus 5 measures the glucose level using a disposable glucose sensor 7, and is provided with a holding part 50, a connector unit 51, a storage unit 52, and a display unit 53. The disposable glucose sensor 7 is a sensor that sucks blood, which is obtained by puncturing the puncture needle to a fingertip, an abdomen or an arm part, and outputs signal indicating the insulin level of the blood. As the glucose sensor 7, the electrode type sensor that produces the response current corresponding to the applied voltage or the optical sensor that grasps the coloration of a reagent layer by light irradiation can be used. The display unit 53 is a unit that displays the glucose level, and contains, for example, LCD. Moreover, the display unit can display the glucose concentration and the measurement time that are measured by the continuous glucose monitoring apparatus 1.

The information processing apparatus 6 is for managing the information related to the glucose level. The information processing apparatus 6 is, for example, a personal computer. This information processing apparatus 6 has a holding part 60, a connector unit 61, and a storage unit 62.

The holding parts 40, 50 and 60 of the external apparatus 4, 5, and 6 are parts to which the data holding unit 3 of the continuous glucose monitoring apparatus 1 is fixed. Each of the holding parts 40, 50, and 60 has structure similar to that of the cover 20A in the sensing unit 2. The holding parts 40, 50 and 60 have concave parts 43, 53 and 63 that are to be engaged with the hooks 30A in the data holding unit 3. The shape of each of the concave parts 43, 53 and 63 is similar to that of the concave parts 20Aa of the case 20 in the sensing unit 2 and the concave parts 43, 53 and 63 is formed at the positions similar to that of the concave parts 20Aa.

The connector units 41, 51, and 61 of the external apparatus 4, 5, and 6 are for transporting the response current value or the glucose concentration corresponding to the response current value stored in the data storage unit 25 to the storage parts 42, 52 and 62 of the external apparatus 4, 5 and 6 through the data holding unit 3. Each of the connector units 41, 51, and 61 has structure similar to that of the connector unit 23 of the sensing unit 2. That is, the connector units 41, 51 and 61 have the pillar-shaped terminals 41A, 51A and 61A and the holders 41B, 51B and 61B. The pillar-shaped terminals 41A, 51A and 61A are members that contact the pin-like terminals 32A of the connector unit 32 in the data holding unit 3, and carry out an electrical connection to the storage units 42, 52 and 62 of the external apparatus 4, 5 and 6. The pillar-shaped terminals 41A, 51A, and 61A are formed by insert molding in a condition the bended platy member formed from a material having high conductivity, such as metal material, carbon material, etc. is inserted into the holder 23B.

The storage parts 42, 52 and 62 of the external apparatus 4, 5 and 6 are units that store, when receiving the response current value or the glucose concentration corresponding to the response current value through the connector units 41, 51 and 61, the received data.

With the glucose level control system X, by setting the data holding unit 3 removed from the continuous glucose monitoring apparatus 1 to any one of the external apparatus 4, 5 and 6, the response current value obtained by the sensing unit 2 using the glucose sensor 22 or the glucose concentration corresponding to the response current value can be migrated to the storage parts 42, 52 and 62 of the external apparatus 4, 5 and 6 through the connecter unit 32 of the data holding unit 32 and the connector units 41, 51 and 61 of the external apparatus 4, 5 and 6.

Here, when the response current value obtained by the glucose sensor 22 of the sensing unit 2 is stored in the data storage unit 34 of the data holding unit 3, to begin with, the response current value stored in the data storage unit 34 of the data holding unit 3 is migrated to the storage unit 52 of the self-monitoring blood glucose apparatus 5. The calculation unit (not shown in the figure) in the display unit 53 of the self-monitoring blood glucose apparatus 5 converts the response current value to the glucose concentration in body fluid using the glucose level measured by the glucose sensor or the calibration equation determined from the glucose level. The calibrated glucose concentration is stored in the data storage unit 34 of the data holding unit 3. Next, the glucose concentration stored in the data storage unit 34 of the data holding unit 3 is migrated to the storage part 62 of the information processing apparatus 6, and it is managed in the information processing apparatus 6. Otherwise, the glucose concentration stored in the data storage unit 34 of the data holding unit 3 is migrated to the storage unit 42 of the insulin dosing apparatus 4, and is used as an argument for determining the insulin quantity to be injected to the body.

On the other hand, when the glucose concentration calculated based on the response current value obtained by the glucose sensor 22 of the sensing unit 2 is stored in the data storage unit 34 of the data holding unit 3, the glucose concentration stored in the data storage unit 34 of the data holding unit 3 is migrated to the storage unit 42 of the insulin dosing apparatus 4, and is used as an argument for determining the insulin quantity to be injected to the body. Or it is moved to the storage part of the information processing apparatus 6, and the glucose concentration memorized by the data storage unit 34 of the data holding unit 3 is managed. Otherwise, the glucose concentration stored in the data storage unit 34 of the data holding unit 3 is migrated to the storage unit 62 of the information processing apparatus 6, and is managed.

Note that, the time information (the time at which response current is sampled, the time at which the data holding unit 3 is separated from the sensing unit 2, the period of time elapsed from the time when the data holding unit 3 is separated from the sensing unit 2, the period of time elapsed from the time when the glucose sensor 22 is exchanged, etc.) measured by the clock unit 27 or the clock unit 36 is also stored in the data storage unit 34 of the data holding unit 3, the time information may be migrated, together with the response current value obtained by the glucose sensor of the sensing unit 2 or the glucose concentration calculated based on it, to the storage parts 42, 52, and 62 of the external apparatus 4, 5, and 6 from the data storage unit 34 of the data holding unit 3. In this case, for example, it is possible to configure the data holding unit 3 or the external apparatus 4, 5 or 6 so as to compare the time information stored in the data storage unit 34 with the current time, and activates an informing means when the difference between them exceeds the predetermined permission time. When the difference between the time information stored in the data storage unit 34 and the current time exceeds the predetermined permission time, the response current value which will be obtained by the glucose sensor 22 at the present time or the glucose concentration calculated based on the response current value may differ significantly from the response current value or the glucose concentration calculated based on the response current value stored in the data storage unit 34. In such a case, if the informing means is activated, the operator of the data holding unit 3 or the external apparatus 4, 5 or 6 can recognize the possibility of the above significant change. Note that, the informing means herein is, for example, a unit that turns on a warning light or generates warning sound. This informing means may be provided in the data holding unit 3 or one of the external apparatus 4, 5 and 6.

By the method in which data transmission between the continuous glucose monitoring apparatus 1 and the external apparatus 4, 5, and 6 is performed in this way, a cable required for the wire communication method is not required. Therefore, problems that "the cable connecting the continuous glucose monitoring apparatus with the insulin dosing apparatus may touch a patient's skin, thereby giving the patient displeasure" and "the cable is caught in the patient's clothes, arm, etc. and is disconnected from the continuous glucose monitoring apparatus or the external apparatus 4, 5 or 6" do not arise. Further, data communication performed by contacting the data holding unit 3 and the external apparatus 4, 5 or 6 through the connector unit 32 and the connector unit, 41, 51 or 61 does not get entangled with the communication data of other communication facilities, such as a cellular phone. Therefore, a possibility that the data is transmitted incorrectly from the continuous glucose monitoring apparatus 1 to the external apparatus 4, 5 or 6 can be reduced. Accordingly, it is possible to transmit data more exactly to the insulin dosing apparatus 4. As a result, it is possible to inject the appropriate quantity of insulin to the patient's body, and to control the glucose level as a desired value. Moreover, since the more exact glucose level etc. can be displayed in the self-monitoring blood glucose apparatus 5, the patient can know the self glucose level more correctly. Furthermore, since the data about the more exact glucose level is managed in the information processing apparatus 6, the patient's glucose level can be controlled more correctly.

The glucose level control system according to the present invention is not limited to the example shown in FIG. 10 and FIG. 11, and may be modified in a variety of forms. For example, it is possible to use, as the connector unit and the engaging means in the data holding unit 3 of the continuous glucose monitoring apparatus 1, those shown in FIG. 7 through FIG. 9 and to use, as the connector unit and the fixing part in each of the external apparatuses 4, 5 and 6, the connector unit and the fixing part of the sensing unit shown in FIG. 7 through FIG. 9.

Although, the above embodiment is the one in which the response current value measured by the sensing unit 2 or the data corresponding to the value is transmitted to the external apparatus 4, 5 or 6 through the data holding unit 3, the present invention can be actualized in a form where data transmission from the external apparatus 4, 5 or 6 to the sensing unit 2 through the data holding unit 3 can also be performed. With this configuration, for example, revising the data about the calibration curvet and/or data for temperature correction stored in the sensing unit 2 can be performed by transmitting revised data from the information processing apparatus to the data holding unit 3, and then migrating the revised data from the data holding unit 3 to the sensing unit 2.

Moreover, the glucose level measured by the glucose sensor 7 of the simple glucose monitoring apparatus 5 or the calibrated equation determined from the glucose level may be transmitted to the sensing unit 2 through the data holding unit 3. In this case, calibration of the response current value obtained by the glucose sensor 22n can be made in theسسsensing unit 2. Therefore, it is possible to lower frequency that information (the response current value obtained by the glucose sensor 22) or data corresponding to the information (the glucose concentration in the body fluid, such as blood or intercellular fluid calculated based on the response current value and the data about the calibration curve) is migrated from the sensing unit 2 to the simple glucose monitoring apparatus 5 through the data holding unit 3.

The present invention can be applied not only for measuring the glucose concentration in the body fluid, such as blood and intercellular fluid, and controlling the glucose concentration in body fluid according to the measured glucose concentration, but also for, for example, measuring concentration of lactic acid or cholesterol, and controlling the concentration.

DESCRIPTION OF THE SYMBOLS AND NUMERALS

X glucose level control system (body fluids component control system)
1, 1', 1" continuation glucose monitering device (continuous analysis apparatus)
2, 2', 2" sensing unit
20Aa, 20Aa" concave part (of the sensing unit) (engaging means)
22 glucose sensor (of the sensing unit) (sensor)
23, 23', 23" connector unit (sensing unit)
3, 3', 3" data holding unit
30A, 30A" hook (of the data holding unit) (engaging means)
32, 32', 32" connector unit (of the sensing unit)
35 data storage unit (storage means)
4 insulin dosing apparatus
40 fixing part (of the insulin dosing apparatus)
41 connector unit (of the insulin dosing apparatus)
42 storage unit (of the insulin dosing apparatus) (storage means)
43 concave part (of the insulin dosing apparatus) (engaging means)
5 self-monitoring blood glucose apparatus
51 connector unit (of the self-monitoring blood glucose apparatus)
52 storage unit (of the self-monitoring blood glucose apparatus) (storage means)
53 concave part (of the self-monitoring blood glucose apparatus) (engaging means)
6 information processing apparatus
61 connector unit (of the information processing apparatus)
62 storage unit (of the information processing apparatus) (storage means)
63 concave part (of the information processing apparatus) (engaging means)
7 disposal glucose sensor

The invention claimed is:
1. A continuous analysis apparatus comprising:
a sensing unit including a subcutaneous sensor for obtaining information with respect to an objective substance in a sample,
a power supply for supplying power to the sensor,
a data storage part for storing information obtained from the sensor; and
a data holding unit joined to or alternatively, separated from the sensing unit, the data holding unit including a storage means, and
a control part, included in the data holding unit, for performing, when the data holding unit is joined to the sensing unit, control of storing the information stored in the data storage part of the sensing unit or data corresponding to the information stored in the data storage part of the sensing unit into the storage means and performing, when the data holding unit is separated from the sensing unit and joined to an external apparatus, control of transmitting to the external apparatus the information stored in the storage means, wherein the sensing unit and the data holding unit each comprise a data communication unit for transmitting data from the sensing unit to the data holding unit or from the data holding unit to the sensing unit, and wherein the external apparatus comprises a data communication unit configured for transmitting data from the external apparatus to the data holding unit or from the data holding unit to the external apparatus via their respective communication units.

2. The continuous analysis apparatus according to claim 1, wherein the sensing unit and the data holding unit each comprise an engaging means for separably joining the data holding unit to the sensing unit.

3. The continuous analysis apparatus according to claim 1, wherein the data communication units of the sensing unit and the data holding unit transmit the data when the sensing unit and the data holding unit are not in contact with each other.

4. The continuous analysis apparatus according to claim 1, wherein the data communication units of the sensing unit and the data holding unit each comprise connector units, wherein the connector units transmit the data when the sensing unit and the data holding unit are in contact with each other.

5. The continuous analysis apparatus according to claim 4, wherein each connector unit is placed in one engaging means, and the data is transmitted by joining the data holding unit to the sensing unit.

6. The continuous analysis apparatus according to claim 4, wherein each engaging means is placed in one connector unit, and the data holding unit is joined to the external apparatus by bringing the data holding unit and the external apparatus into contact.

7. A control system comprising the continuous analysis apparatus according to claim 1 and the external apparatus, wherein the external apparatus has a storage means for storing the information from the data holding unit, and the data holding unit and the external apparatus are joined together or alternatively, separated from each other.

8. The control system according to claim 7, wherein the external apparatus and the data holding unit each comprise an engaging means for separably joining the data holding unit to the external apparatus.

9. The control system according to claim 7, wherein the data communication units of the external apparatus and the data holding unit transmit the data when the external apparatus and the data holding unit are not in contact with each other.

10. The control system according to claim 7, wherein the data communication units of the external apparatus and the data holding unit each comprise a connector unit, wherein the connector units transmit the data when the external apparatus and the data holding unit are in contact with each other.

11. The control system according to claim 10, wherein each connector unit is placed in one engaging means, and the data is transmitted by joining the data holding unit to the external apparatus.

12. The control system according to claim 10, wherein each engaging means is placed in one connector unit, and the data holding unit is joined to the external apparatus by bringing the data holding unit and the external apparatus into contact.

13. The control system according to claim 7, wherein the external apparatus connector unit is installed in the engaging means, wherein the external apparatus is a medicine dosing apparatus for dosing medicine into a body, an information processing apparatus for managing information related to a sample component, or a display unit for displaying a concentration of a sample component.

* * * * *